(12) United States Patent
Jiyan et al.

(10) Patent No.: US 6,683,304 B1
(45) Date of Patent: Jan. 27, 2004

(54) METHOD FOR A PLAN-VIEW TRANSMISSION ELECTRON MICROSCOPY SAMPLE PREPARATION TECHNIQUE FOR VIA AND CONTACT CHARACTERIZATION

(75) Inventors: Dai Jiyan, Hong Kong (HK); Tee Siam Foong, Johor Bahru (MY); Tai Chui Lam, Johor Bahru (MY); Eddie Er, Johor Bahru (MY); Shailesh Redkar, Singapore (SG)

(73) Assignee: Chartered Semiconductor Manufacturing Limited, Singapore (SG)

( * ) Notice: Subject to any disclaimer, the term of this patent is extended or adjusted under 35 U.S.C. 154(b) by 0 days.

(21) Appl. No.: 10/192,751

(22) Filed: Jul. 8, 2002

(51) Int. Cl.$^7$ .......................... G01N 23/00; G21K 7/00
(52) U.S. Cl. .................................. 250/307; 250/311
(58) Field of Search ........................ 250/307, 306, 250/311, 492.21, 442.11, 310

(56) References Cited

U.S. PATENT DOCUMENTS

| | | | |
|---|---|---|---|
| 5,977,543 A | * 11/1999 | Ihn et al. | 250/311 |
| 6,042,736 A | * 3/2000 | Chung | 216/33 |
| 6,194,720 B1 | * 2/2001 | Li et al. | 250/311 |
| 6,300,631 B1 | * 10/2001 | Shofner | 250/311 |
| 6,496,559 B1 | * 12/2002 | Morken | 378/58 |
| 6,497,194 B1 | * 12/2002 | Libby et al. | 118/723 FI |

* cited by examiner

Primary Examiner—Bruce Anderson
Assistant Examiner—Johnnie L Smith, II

(57) ABSTRACT

A method for preparing a transmission electron microscopy (TEM) sample for contact and via characterization. Specifically, one embodiment of the present invention discloses a method where an integrated circuit semiconductor chip (IC chip) is bonded to a piece of glass and attached to a sample holder. Areas of the IC chip are removed by polishing until a region surrounding a particular contact or via is exposed. The piece of glass supports the IC chip during the polishing process. The IC chip is cut using a focused ion beam to create a thin membrane suitable for TEM failure analysis. The thin membrane includes a plan-view cross-section from the particular contact or via. The cross-sectional plan-view is perpendicular to the longitudinal axis of the contact or via.

21 Claims, 5 Drawing Sheets

METHOD FOR A PLAN-VIEW TRANSMISSION ELECTRON MICROSCOPY SAMPLE PREPARATION TECHNIQUE FOR VIA AND CONTACT CHARACTERIZATION

BACKGROUND OF THE INVENTION

1. Field of the Invention

The present invention relates to the field of failure analysis in semiconductor manufacturing. Specifically, the present invention relates to the field of transmission electron microscopy sample preparation for failure analysis in semiconductor manufacturing.

2. Related Art

Failure analysis and sample preparation is an important tool in providing a detailed inspection of the physical characteristics of an integrated circuit (IC) fabricated on a semiconductor chip (IC chip). With the structure of integrated circuits decreasing in size and becoming more complex, transmission electron microscopy has emerged as a critical tool for highly site-specific failure analysis. More particularly, an important issue is the analysis of via and contact failure between layers in an integrated circuit. That is, contact and via failure analysis is one of the most common inspections in semiconductor manufacturing.

Physical characteristics of via and contact plugs provide critical factors in determining the overall performance of an IC chip. These physical characteristics are directly linked to the properties related to electrical conductivity of the via and contact plug. The most critical factors for via and contact properties include barrier metal layer coverage and plug critical dimensions, hereinafter referred to as "CD".

Conventional transmission electron microscopy, hereinafter referred to as "TEM", sample preparation techniques cut along the longitudinal axis of a via or contact using a focused ion beam, hereinafter referred to as "FIB". This TEM inspection along or parallel to the longitudinal axis is the most widely used method to evaluate via and contact characteristics.

FIG. 1 illustrates the conventional TEM sample preparation technique used for cutting along the longitudinal axis with an FIB in the prior art. The IC chip 110 is placed on a sample holder 130. The sample holder 130 is suitable for interfacing with an FIB sample holder (not shown) in order to orient the sample for cutting with the FIB.

Continuing with FIG. 1, the IC chip 110 is oriented such that the top layer of the IC chip 110 is exposed to the FIB 120. The FIB 120 is perpendicular to the top and all underlying layers of the IC chip 110 in FIG. 1. Electrical conduits, such as vias and contacts, provide electrical conduction paths between layers in the IC chip 110. As such, the FIB 120 cuts down through the IC chip 110 parallel to the longitudinal axis of a via or contact plug. By proper displacement of the FIB, a TEM sample membrane suitable for TEM failure analysis can be prepared for examining the critical dimensions of the via or contact plug.

However, the difficulties associated with cutting to the plug center using conventional techniques make measurement of the barrier thickness and the plug's critical dimensions inaccurate. Accuracy of these measurements is affected both by the thickness of the TEM sample and the diminution of the via and contact plugs in order to build smaller IC chips.

For example, the thickness of the TEM sample makes cutting to the center of the plug impossible. A TEM sample cut parallel to the longitudinal axis creates a rectangular cross-sectional view of the plug that does not include a view of the center cross-section of the plug. This is because the TEM sample has a measurable thickness.

The center cross-section plug is a plane that includes the longitudinal axis. This center cross-section gives the best view of the plug for TEM analysis. However, the thickness of the TEM sample has an adverse affect when dealing with the decreasing physical dimensions of the contact or via plugs. In some cases, the TEM sample thickness is up to two-thirds of that of the center diameter of the plug. An adequate TEM sample showing the center cross-section of the plug is difficult to prepare using conventional techniques because of the thickness of the ion beam. Further, measurement of the critical dimensions from a TEM sample, that does not show the center cross-section plug, is difficult.

Additionally, the shielding effect due to the sample thickness and circular shape of the plug has an adverse affect when measuring the thickness of the barrier liner walls. A resulting TEM sample cut using an FIB is not uniform due to the curvature of the plug walls. This non-uniformity along with the thickness of the TEM sample introduces shielding or shadowing effects. The shadowing effect is more pronounced the further the FIB cut is made away from the center of the plug. Measurement of the barrier thickness under TEM analysis is impossible with pronounced shadowing or shielding effects.

Thus, a need exists for a preparation technique that provides better via and contact characterization for failure analysis. A further need exists for a preparation technique that provides for more accurate measurement of the physical dimensions of the via and contact plugs.

SUMMARY OF THE INVENTION

The present invention provides a method for providing transmission electron microscopy sample preparation of an integrated circuit prepared on a semiconductor chip wherein the method provides better via and contact characterization for failure analysis. Also, the present invention provides a method that achieves the above accomplishment and which also provides for more accurate measurement of the physical dimensions of the via and contact plugs.

Specifically, the present invention discloses a method for preparing a transmission electron microscopy (TEM) sample for contact and via characterization. One embodiment of the present invention discloses a method where an integrated circuit semiconductor chip, e.g., IC chip, is bonded to a piece of glass and attached to a sample holder. Areas of the IC chip are removed by polishing until a region surrounding a particular contact or via is exposed. The piece of glass supports the IC chip during the polishing process. The IC chip is cut using a focused ion beam (FIB) to create a thin membrane suitable for TEM analysis. The thin TEM sample membrane includes a plan-view cross-section from the particular contact or via. The cross-sectional plan-view is perpendicular to the longitudinal axis of the contact or via.

In another embodiment, the present invention provides a method for preparing a TEM sample membrane that includes multiple contacts or vias. The thin membrane of the TEM sample includes plan-view cross-sections of each of the multiple contacts or vias contained within the TEM sample. Each of the plan-view cross-sections is perpendicular to the longitudinal axis for each contact or via in the thin membrane suitable for TEM analysis.

These and other objects and advantages of the present invention will no doubt become obvious to those of ordinary skill in the art after having read the following detailed description of the preferred embodiments which are illustrated in the various drawing figures.

BRIEF DESCRIPTION OF THE DRAWINGS

PRIOR ART

DETAILED DESCRIPTION OF THE INVENTION

Reference will now be made in detail to the preferred embodiments of the present invention, a method for a plan-view transmission electron microscopy sample preparation technique for via and contact characterization, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims.

Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, components, and circuits have not been described in detail as not to unnecessarily obscure aspects of the present invention.

Accordingly, the present invention discloses a method for a preparation technique for providing a transmission electron microscopy (TEM) sample of an integrated circuit semiconductor chip (IC chip) that gives better via and contact characterization for failure analysis. Also, the present invention provides a method that achieves the above accomplishment and which also provides for more accurate measurement of the physical dimensions of the via and contact plugs.

Figure 1:
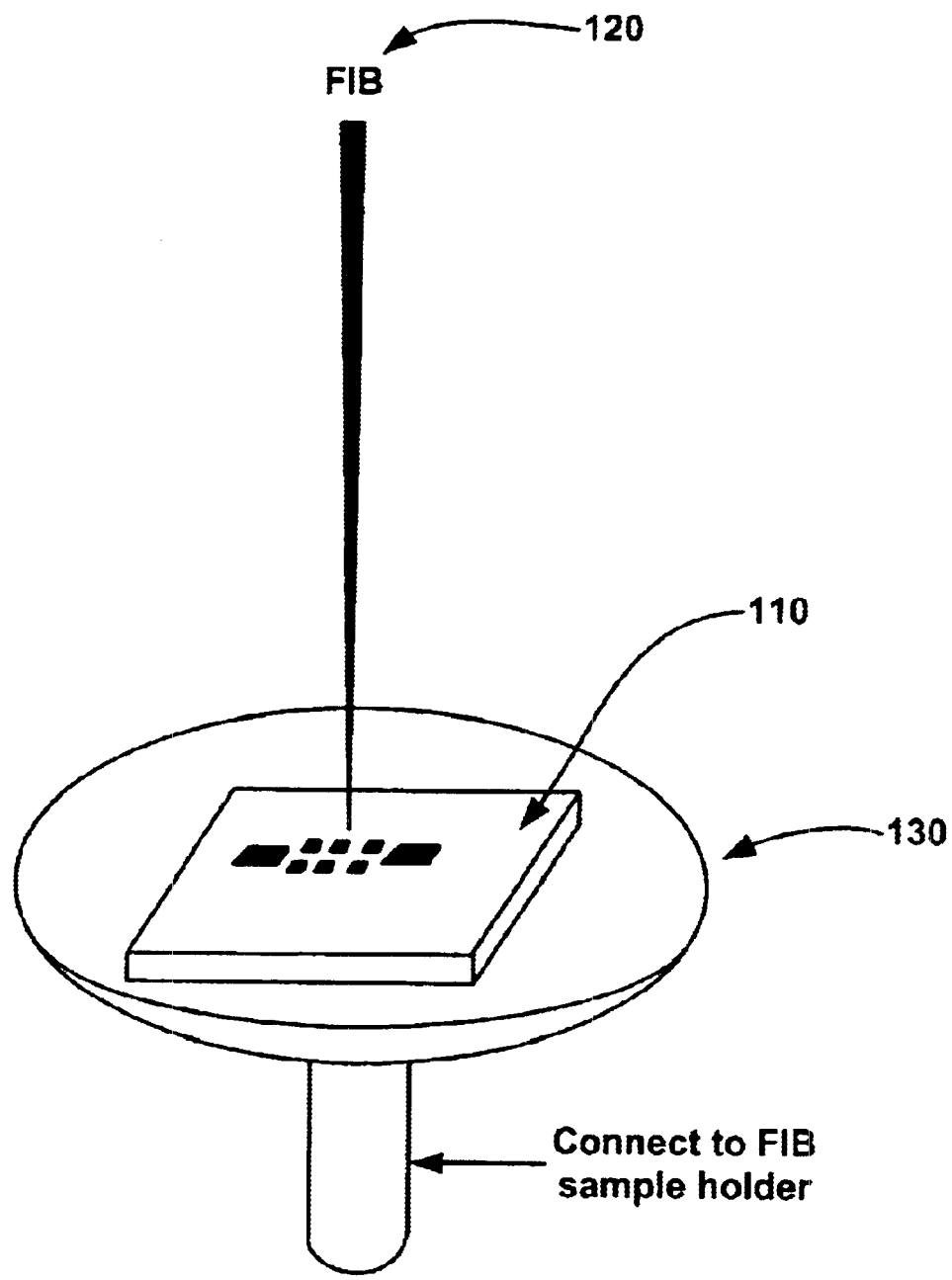
FIG. 1 illustrates a conventional TEM sample preparation by a focused ion beam in semiconductor failure analysis.
Figure 2:
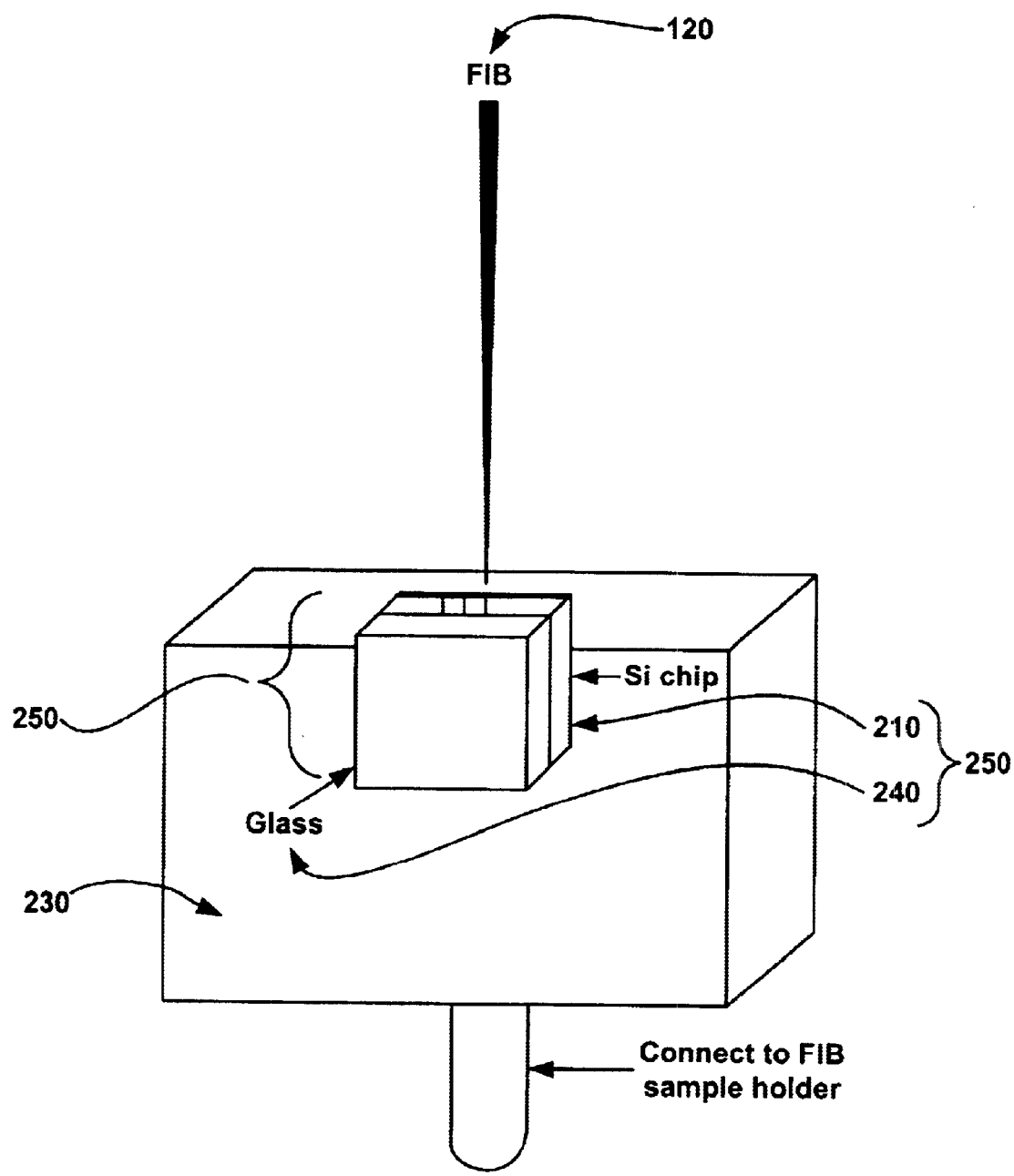
FIG. 2 illustrates a TEM sample block oriented to cut cross-sectionally across an electrical conduit-by a focused ion beam to create a plan-view cross-section TEM sample membrane, in accordance with one embodiment of the present invention.

FIG. 2 illustrates the preparation of a TEM sample membrane by a focused ion beam that provides for a plan-view cross-section of the contact or via plug, in accordance with one embodiment of the present invention. The resulting TEM sample membrane is used for TEM failure analysis of the IC chip 210. In FIG. 2, the IC chip 210 is bonded to a piece of glass 240 to form a sample block 250. The glass 240 supports the IC chip 210 throughout each of the steps of the technique used in preparing the TEM sample. More specifically, the glass 240 supports the IC chip during the polishing of the sample block 250 and the IC chip 210.

FIG. 2 also shows that the sample block 250 is attached to a sample holder 230. In one embodiment of the present invention, the IC chip 210 is adjacent to both the glass 240 and the sample holder 230. In other words, the IC chip 210 is sandwiched between the glass 240 and the sample holder 230.

Furthermore, the sample holder 230 is oriented in such a way to accommodate a focused ion beam (FIB) 120 to make a cross-sectional cut that is perpendicular to the longitudinal axis of the contact or via plug. This cut allows for TEM sample membrane preparations that include a plan-view cross-section of contacts and vias.

Figure 3:
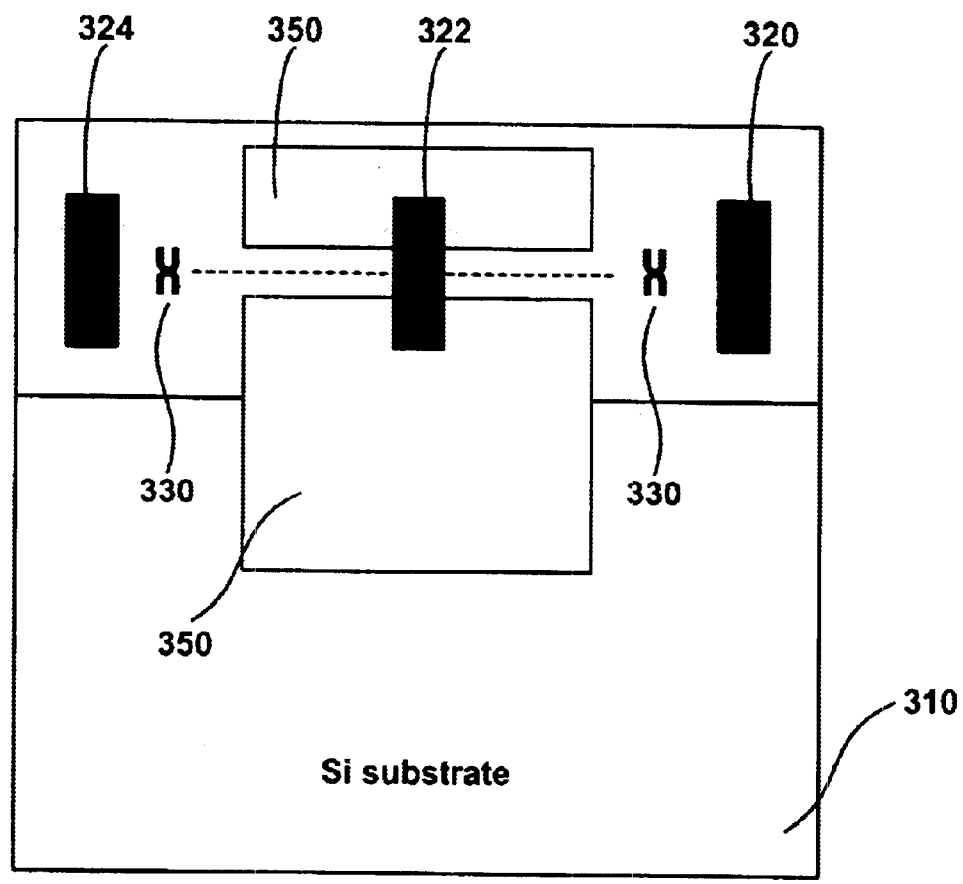
FIG. 3 illustrates a side view of the electrical conduits and the focused ion beam cut, in accordance with one embodiment of the present invention.

FIG. 3 illustrates a side view of the electrical conduits that are contacts and/or vias, in accordance with one embodiment of the present invention. FIG. 3 also shows the linear displacement of a focused ion beam cut. A silicon substrate 310 provides a base for the IC chip, such as IC chip 210, that contains the electrical conduits 320, 322, and 324. It is appreciated that electrical conduits 320, 322, and 324 may be vias or contacts.

Contacts and vias are identical in their characterization, form, and use. The distinction between the two electrical conduits lies in their particular placement within the IC chip. A contact provides an electrical conduit between two metal layers in an IC chip. A via provides an electrical conduit between a metal layer and a semiconductor device in the IC chip. At their core, the contact and via electrical conduits are typically formed from tungsten plugs. Surrounding the plugs may be protective barrier liners.

The electrical conduits, such as vias and contacts, typically are cylindrical in shape. A longitudinal axis extends from one end of the electrical conduit to the other end of the conduit through the center of the conduit. The longitudinal axis also extends through the center of the plug that defines the electrical conduit. It is appreciated that the electrical conduits can be of any shape and form.

Continuing with FIG. 3, a particular electrical conduit 322, is shown to illustrate the technique used to obtain a plan-view cross-section of the electrical conduit 322. Electrical conduit 322 may be a contact or a via. FIG. 3 also shows milled blocks 350 that are cut to isolate the region surrounding the electrical conduit 322.

Line X—X 330 in FIG. 3 illustrates the line through which an FIB cut is made to prepare a TEM sample membrane. Preparation of the TEM sample membrane may require more than one cut. The resulting TEM sample membrane contains a plan-view cross-section of the electrical conduit 322 that is perpendicular to the conduit's longitudinal axis. The plan-view cross-section is approximately circular in shape in this embodiment; however, it is appreciated that the plan-view cross-section can be of any shape or form.

It is appreciated that FIG. 3 is exemplary only and that an IC chip contains any number of contacts and vias connecting any number of metal layers and semiconductor devices.

Figure 4B:
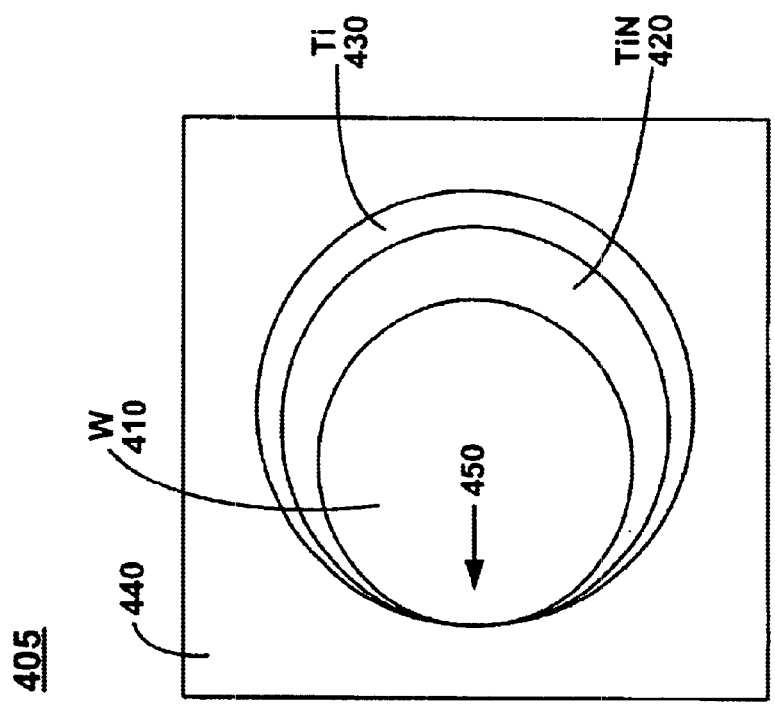
FIG. 4b illustrates a top view of a TEM sample membrane containing a circular cross-section of the via or contact that shows imperfections in the barrier thickness, in accordance with one embodiment of the present invention.
Figure 4A:
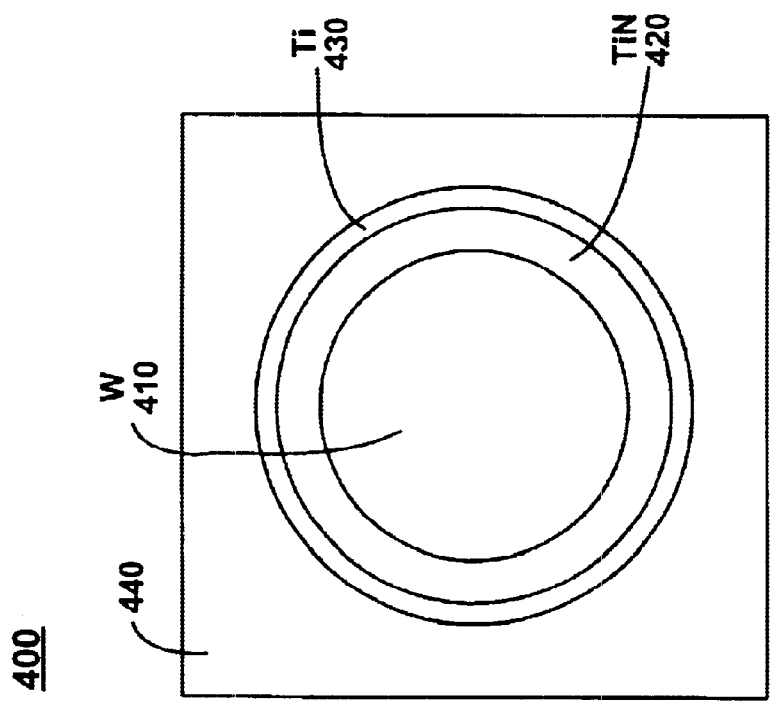
FIG. 4a illustrates a top-view of a TEM sample membrane containing a circular cross-section of the via or contact, in accordance with one embodiment of the present invention.

FIG. 4a illustrates a top or plan-view of an exemplary TEM sample membrane 400 containing a circular cross-section of the electrical conduit 322, in accordance with one embodiment of the present invention. FIG. 4a illustrates that the electrical conduit 322 is comprised of a plug and two barrier liners. In one example, as illustrated in FIG. 4a, the TEM sample membrane 400 shows no critical failures in the formation of the plug and barrier liner walls for the cross-section taken along line X—X 330 of the electrical conduit 322.

A tungsten plug 410 is shown in FIG. 4a to be circular in shape. A barrier liner of titanium nitride (TiN) 420 is shown. Also a barrier liner of titanium (Ti) 430 is shown. The barrier liners are formed to help with tungsten nucleation and to prevent the diffusion of the metal plug, e.g., $WF_6$, from leaching into the dielectric layer 440. The dielectric layer 440, for example, can be an inter-metal dielectric (IMD) or an inter-layer dielectric (ILD).

FIG. 4b illustrates a top or plan-view of an exemplary TEM membrane 405 containing a circular cross-section of the electrical conduit 322, in accordance with another embodiment of the present invention. In another example, as illustrated in FIG. 4b, the TEM membrane 400 shows failures in the formation of the plug and barrier liner walls.

For example, failures in the TiN barrier liner 420 and the Ti barrier liner 430 are shown in FIG. 4b. The barrier liners 420 and 430 fail to separate the tungsten plug 410 from the IMD/ILD layer 440 at the point illustrated by arrow 450. Depending of the severity of the failure, the conductive properties associated with the electrical conduit 322 from which TEM sample 405 was taken may be adversely affected. Additionally, this failure may affect the overall performance of the IC chip containing the electrical conduit 322.

FIGS. 4 and 4a illustrate the positive benefits of taking plan-view cross-sectional TEM sample membranes. Since the TEM samples are cut with an FIB perpendicular to the longitudinal axis of the via or contact, the shielding and shadowing effects due to the sample thickness and circular shape are eliminated. This is because the interface of barrier to IMD/ILD and W plug is edge on. In other words, the circular shape of the barrier liner does not introduce any shadowing or shielding effects since the barrier liner is uniform throughout from the front to the back of the TEM sample membrane in a plan-view cross-section. Also, a full and unobstructed view of the plug and barrier liners is possible.

Therefore, measurement of the barrier thickness, such as, for TiN liner 420 and Ti liner 430 will be very accurate. In addition, the critical dimensions of the W plug 410 can be accurately measured. Further, inconsistencies in plug or barrier liner formation is readily shown using the techniques illustrated in embodiments of the present invention. This new TEM sample preparation technique of creating a plan-view cross-section using an FIB in accordance with the present invention will, therefore, provide accurate measurement and consistent characterization of vias and contacts.

Also, this TEM sample preparation technique can also be used to characterize the structural properties of formations, such as, salicide or poly-silicon, in the semiconductor chip. These structural properties include, but are not limited to the following: grain size, grain texture, grain distribution, interface dynamics, and phase identification, etc.

In one embodiment of the present invention, the method for cutting a TEM sample membrane perpendicularly to the longitudinal axis of the via or contact includes a sample holder 230 as shown in FIG. 2. It is appreciated that the sample holder 230 is any sample holder capable of supporting an IC chip throughout the preparation process, including the polishing of the IC chip and the cutting of the chip using an FIB. Also, the sample holder 230 is able to interface with an FIB sample holder for placing into the FIB chamber.

The sample holder 230 is oriented such that the attached silicon block 250 containing the IC chip 210 is exposed to polishing. The IC chip 210 is bonded to a piece of glass 240 for support during the polishing process. The polishing removes areas of the IC chip 210 in order to expose a region surrounding a particular electrical conduit. Typically, the remaining region is one to five micrometers from the specific via or contact of interest.

In one embodiment of the present invention, the polishing is done parallel to the longitudinal axis of the via or contact. In other words, the direction of polishing proceeds from the sidewall of the silicon chip 210 towards the center of the silicon wafer. Instead of removing single layers of the IC chip, areas of the IC chip 210 that contain multiple layers are removed. This is possible since the IC chip 210 is supported by the glass 240 for more stability during the polishing process.

Next, the sample holder 230 with the side polished IC chip 210 is loaded into an FIB chamber. Micro-anatomy can then be performed on the side polished surface to make a TEM sample membrane containing a plan-view of the circular shaped tungsten (W) plugs, as described in the previous paragraphs (see FIGS. 4a and 4b). As is typically done, this TEM sample membrane is then picked up by a glass needle using a manipulator and loaded on a TEM copper grid coated with Formvar film for TEM failure analysis.

Figure 5:
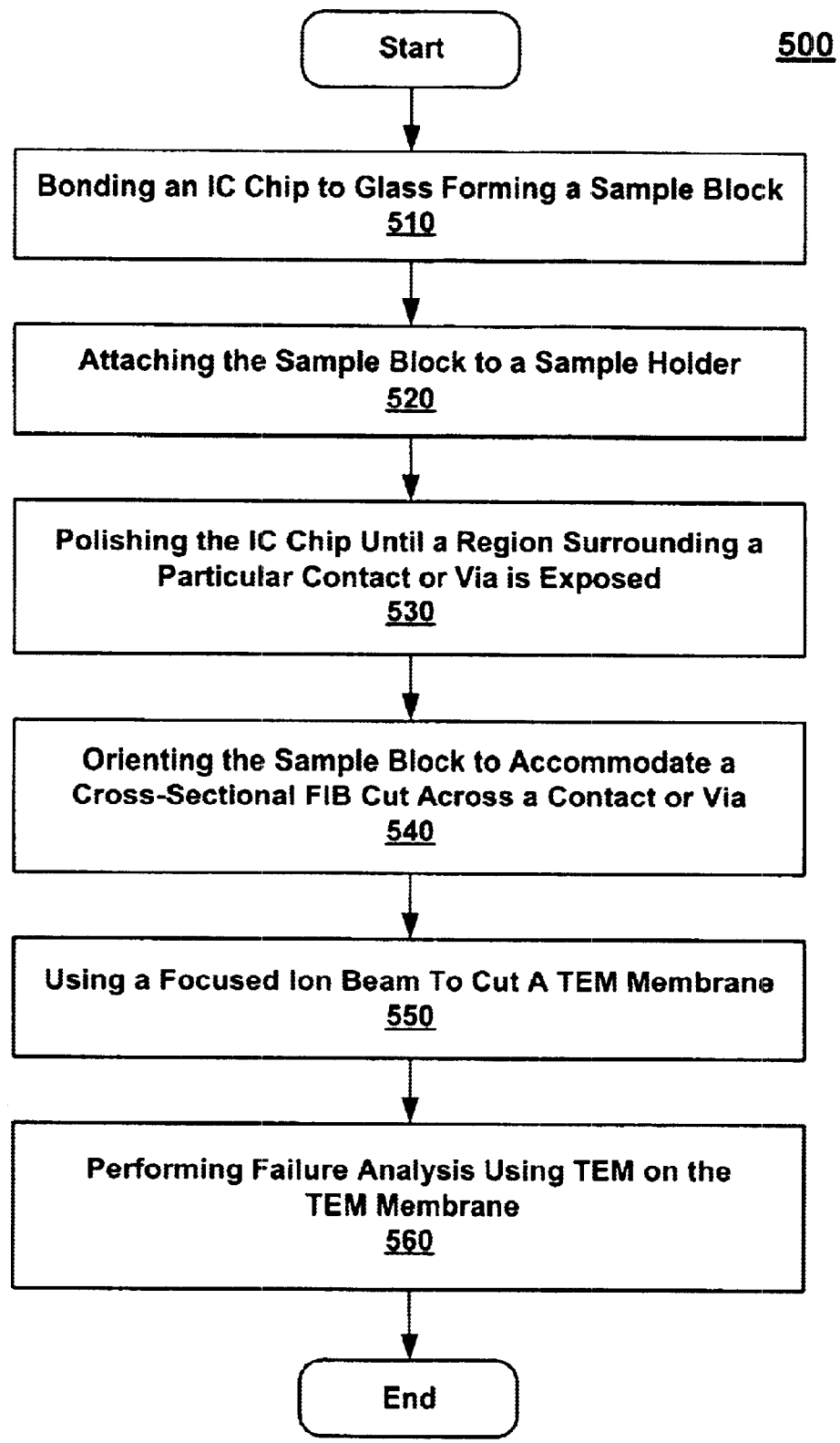
FIG. 5 is a flow diagram illustrating steps in a method for preparing a TEM sample membrane that includes a plan-view cross-sectional cut of a contact or via, in accordance with one embodiment of the present invention.

FIG. 5 illustrates an exemplary flow chart 500 for preparing a TEM sample membrane that contains a plan-view cross-section of the electrical conduit, in accordance with one embodiment of the present invention. Flow chart 500 begins in step 510 by bonding an IC chip to a piece of glass in order to form a sample block. The sample block is then attached to a sample holder in step 520.

Continuing with FIG. 5, the method then removes areas of the IC chip until a region surrounding a first electrical conduit is exposed, in step 530. In one embodiment, the removal process includes polishing, grinding, milling with an FIB, or any typical removal process used in failure analysis of semiconductor manufacturing.

The electrical conduit can be a via or a contact. Also, it is appreciated that the IC chip may have a plurality of electrical conduits. In each case, each of the plurality of electrical conduits is approximately cylindrical in shape with two opposing ends. Also, a longitudinal axis extends between the two opposing ends of the electrical conduit.

In step 540 of flow chart 500, the sample block containing the IC chip and the glass is oriented to accommodate a plan-view cross-sectional cut using an FIB across a contact or via. A sample holder aids in correctly orienting the sample block within the FIB chamber. The plan-view cross-sectional cut is perpendicular to the longitudinal axis of the contact or via of interest.

In step 550 of flow chart 500, the IC chip is cut using a focused ion beam (FIB) to prepare a thin membrane. The FIB cut is perpendicular to the longitudinal axis of the contact or via. Repeated cuts may be necessary to prepare a thin membrane suitable for TEM analysis. The thin membrane includes the plan-view cross-section of the specific contact or via under inspection.

Finally, in step 560, failure analysis using TEM is performed on the TEM sample membrane. In one embodiment, measurements of the critical dimensions of the electrical conduit, the contact or via, is made.

The method as described in flow chart 500 can also be applied to the analysis of multiple vias or contacts. In this case, the TEM sample membrane includes cross-sections from each of a group of electrical conduits that are contacts or vias. This group of electrical conduits is a subset of the plurality of electrical conduits, contacts and vias, contained within the IC chip. The TEM sample membrane would include plan-view cross-sections of each of the contacts and vias contained within the group of electrical conduits.

The preferred embodiment of the present invention, a method for a plan-view TEM sample preparation technique for via and contact characterization, is thus described. While the present invention has been described in particular embodiments, it should be appreciated that the present invention should not be construed as limited by such embodiments, but rather construed according to the below claims.

What is claimed is:

1. A method for preparing a transmission electron microscopy (TEM) sample, comprising the steps of:
   removing areas of an integrated circuit semiconductor chip (IC chip) until a region surrounding a first electrical conduit is exposed, said IC chip having a plurality of electrical conduits including said first electrical conduit, each of said plurality of electrical conduits having a first end connected to a second end, and a longitudinal axis extending between said first and second ends; and
   cutting said IC chip using a focused ion beam (FIB) to create a thin membrane suitable for TEM failure analysis, said thin membrane including a plan-view cross-section from said first electrical conduit that is perpendicular to said longitudinal axis of said first electrical conduit.

2. The method as described in claim 1, comprising the further steps of:
   bonding said IC chip to a piece of glass to form a sample block; and
   attaching said sample block to a sample holder, said sample holder adjacent to said IC chip of said sample block.

3. The method as described in claim 2, comprising the further step of:
   orienting said sample block using said sample holder to accommodate a cross-sectional cut using said FIB perpendicular to said longitudinal axis.

4. The method as described in claim 2, wherein said step of removing includes the further step of:
   polishing said sample block and said IC chip parallel to said longitudinal axis, said piece of glass for supporting said IC chip during said polishing.

5. The method as described in claim 1, wherein said first conduit is a via, said via having said first end coupled to a first metal layer and a second end coupled to a second metal layer.

6. The method as described in claim 1, wherein said first conduit is a contact, said contact having said first end coupled to a first metal layer and said second end coupled to a semiconductor device.

7. The method as described in claim 1 comprising the further step of:
   performing TEM analysis on said thin membrane.

8. The method as described in claim 1, wherein said thin membrane includes plan-view cross-sections from each of a group of electrical conduits, said group of electrical conduits taken from said plurality of electrical conduits, said group of electrical conduits including said first conduit.

9. The method as described in claim 8 comprising the further step of:
   performing TEM failure analysis on said thin membrane.

10. A method for preparing a transmission electron microscopy (TEM) sample, comprising the steps of:
    bonding a semiconductor chip (IC chip) to a piece of glass to form a sample block, said IC chip having a plurality of electrical conduits including a via, said via having a first end, a second end, and a longitudinal axis extending between said first and second ends, said first end coupled to a first metal layer and said second end coupled to a second metal layer;
    attaching said sample block to a sample holder, said sample holder adjacent to said IC chip of said sample block;
    removing areas of said IC chip until a region surrounding said via is exposed; and
    cutting said IC chip using a focused ion beam (FIB) to create a thin membrane suitable for TEM failure analysis, said thin membrane including a plan-view cross-section from said via that is perpendicular to said longitudinal axis.

11. The method as described in claim 10 comprising the further step of:
    orienting said sample block using said sample holder to accommodate a cross-sectional cut using said FIB perpendicular to said longitudinal axis.

12. The method as described in claim 10 comprising the further step of:
    polishing said sample block and said IC chip parallel to said longitudinal axis, said piece of glass for supporting said IC chip during said polishing.

13. The method as described in claim 10 comprising the further step of:
    performing TEM analysis on said thin membrane.

14. The method as described in claim 10, wherein said thin membrane includes plan-view cross-sections from each of a group of electrical conduits, said group of electrical conduits taken from said plurality of electrical conduits, said group of electrical conduits including said via.

15. The method as described in claim 14 comprising the further step of:
    performing TEM failure analysis on said thin membrane.

16. A method for preparing a transmission electron microscopy (TEM) sample, comprising the steps of:
    bonding a semiconductor chip (IC chip) to a piece of glass to form a sample block, said IC chip having a plurality of electrical conduits including a contact, said contact having a first end, a second end, and a longitudinal axis extending between said first and second ends, said first end coupled to a first metal layer and said second end coupled to a semiconductor device;
    attaching said sample block to a sample holder, said sample holder adjacent to said IC chip of said sample block;
    removing areas of said IC chip until a region surrounding said contact is exposed; and
    cutting said IC chip using a focused ion beam (FIB) to create a thin membrane suitable for transmission electron microscopy (TEM) analysis, said thin membrane including a plan-view cross-section from said contact that is perpendicular to said longitudinal axis of said contact.

17. The method as described in claim 16 comprising the further step of:

orienting said sample block using said sample holder to accommodate a cross-sectional cut using said FIB perpendicular to said longitudinal axis.

18. The method as described in claim 16 comprising the further step of:

polishing said sample block and said IC chip parallel to said longitudinal axis, said piece of glass for supporting said IC chip during said polishing.

19. The method as described in claim 16, comprising the further step of:

performing TEM analysis on said thin membrane.

20. The method as described in claim 16, wherein said thin membrane includes plan-view cross-sections from each of a group of electrical conduits, said group of electrical conduits taken from said plurality of electrical conduits, said group of electrical conduits including said via.

21. The method as described in claim 20 comprising the further step of:

performing TEM failure analysis on said thin membrane.

* * * * *

UNITED STATES PATENT AND TRADEMARK OFFICE
CERTIFICATE OF CORRECTION

PATENT NO. : 6,683,304 B1
APPLICATION NO. : 10/192751
DATED : January 27, 2004
INVENTOR(S) : Jiyan et al.

It is certified that error appears in the above-identified patent and that said Letters Patent is hereby corrected as shown below:

On the Title sheet, item 75 inventor Delete "Tai Chui Lam" replace with --Tay Chui Lam--

Signed and Sealed this

Sixteenth Day of January, 2007

JON W. DUDAS
*Director of the United States Patent and Trademark Office*